United States Patent
Hung et al.

(10) Patent No.: US 10,940,554 B2
(45) Date of Patent: Mar. 9, 2021

(54) PLANAR FABRICATION OF MICRO-NEEDLES

(71) Applicant: International Business Machines Corporation, Armonk, NY (US)

(72) Inventors: Li-Wen Hung, Mahopac, NY (US); Jui-Hsin Lai, White Plains, NY (US); Chia-Yu Chen, White Plains, NY (US); Ko-Tao Lee, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 81 days.

(21) Appl. No.: 16/205,296

(22) Filed: Nov. 30, 2018

(65) Prior Publication Data
US 2020/0171593 A1    Jun. 4, 2020

(51) Int. Cl.
| | |
|---|---|
| *B23K 1/00* | (2006.01) |
| *A61B 5/00* | (2006.01) |
| *A61B 5/1473* | (2006.01) |
| *A61B 5/15* | (2006.01) |
| *B23K 101/36* | (2006.01) |
| *A61B 5/145* | (2006.01) |

(52) U.S. Cl.
CPC .......... *B23K 1/0008* (2013.01); *A61B 5/1473* (2013.01); *A61B 5/150984* (2013.01); *A61B 5/685* (2013.01); *A61B 5/14532* (2013.01); *A61B 2562/12* (2013.01); *B23K 2101/36* (2018.08)

(58) Field of Classification Search
CPC ............... B23K 1/0008; B23K 1/0016; B23K 2101/36–42; A61B 5/685; A61B 5/1473; A61B 5/150984; A61B 5/14532; A61B 2562/12; A61B 5/150282; A61B 5/150022; A61M 2037/0053
USPC .................. 228/179.1–180.22, 155, 245–262
See application file for complete search history.

(56) References Cited

U.S. PATENT DOCUMENTS

| | | |
|---|---|---|
| 6,312,612 B1 | 11/2001 | Sherman et al. |
| 6,334,856 B1 | 1/2002 | Allen et al. |
| 6,406,638 B1 | 6/2002 | Stoeber et al. |

(Continued)

OTHER PUBLICATIONS

Dahlmann, G.W., et al., "MEMS High Q Microwave Inductors Using Solder Surface Tension Self-Assembly," 2001 IEEE MTT-S Digest, pp. 329-332.

(Continued)

*Primary Examiner* — Kiley S Stoner
(74) *Attorney, Agent, or Firm* — Scully, Scott, Murphy & Presser, P.C.; Daniel P. Morris (57) ABSTRACT

Methods of fabricating a probe are described. In an example, a structure may be formed on a surface of a substrate. The structure may include the probe, a hinge, and an anchor arranged linearly, where an angle is formed between the probe and the hinge. The hinge may be positioned between the probe and the anchor, and the structure may be parallel to the substrate. An amount of solder may be deposited on an area of the structure that spans from a portion of the probe to a portion of the anchor, and across the hinge. The deposited solder may be reshaped by an execution of a solder reflow process. The reshape of the deposited solder may cause the probe to rotate about the hinge in order to reduce the angle between the probe and the hinge.

20 Claims, 6 Drawing Sheets

(56) References Cited

U.S. PATENT DOCUMENTS

| | | | |
|---|---|---|---|
| 7,785,459 B2 | 8/2010 | Raju et al. | |
| 8,093,628 B2 | 1/2012 | Yang et al. | |
| 2008/0009763 A1 | 1/2008 | Chiou et al. | |
| 2008/0122465 A1 | 5/2008 | Runge et al. | |
| 2009/0326441 A1 | 12/2009 | Iliescu et al. | |
| 2010/0324392 A1* | 12/2010 | Yee | A61B 5/0022 600/345 |
| 2011/0021996 A1 | 1/2011 | Lee et al. | |
| 2011/0073560 A1 | 3/2011 | Yeshurun et al. | |
| 2011/0144467 A1* | 6/2011 | Yao | A61B 5/685 600/373 |
| 2011/0288574 A1* | 11/2011 | Curry | A61B 5/15087 606/185 |
| 2015/0080684 A1* | 3/2015 | Frey | A61B 5/14503 600/309 |
| 2017/0307656 A1* | 10/2017 | Vallauri | G01R 1/0408 |
| 2019/0143091 A1* | 5/2019 | Sakaguchi | A61B 5/0408 600/372 |
| 2019/0366068 A1* | 12/2019 | Li | G03F 7/0035 |
| 2020/0009364 A1* | 1/2020 | Amir | A61K 9/0021 |

OTHER PUBLICATIONS

Ma, B., et al., "A PZT Insulin Pump Integrated with a Silicon Micro Needle Array for Transdermal Drug Delivery," 2006 Electronic Components and Technology Conference, pp. 677-681.

Perennes, F., et al., "Sharp beveled tip hollow microneedle arrays fabricated by LIGA and 3D soft lithography with polyvinyl alcohol," Journal of Micromechanics and Microengineering, Received Aug. 29, 2005, Published Jan. 25, 2006, pp. 473-479, vol. 16.

\* cited by examiner

PLANAR FABRICATION OF MICRO-NEEDLES

BACKGROUND

The present application relates to a fabrication process. More particularly, the present application relates to using a planar approach to fabricate micro-needles.

In some examples, integrated systems designed for specific applications may include micro-needles embedded or attached with components such as electronics, sensors, micro-fluidic channels, and/or other components. For example, medicated adhesive patches may include an array of micro-needles embedded with electronic components configured for biometrics detection and analysis. A fabrication of these micro-needles based on a top-down etching approach may limit a flexibility to produce a plurality of micro-needles embedded with different components.

SUMMARY

In some examples, a method of forming a probe is generally described. The method may include forming a structure that may include a probe, a hinge, and an anchor arranged linearly. The probe and the hinge may be on top of a layer of sacrificial material. The layer of sacrificial material may be on top of a surface of a substrate. The anchor may be disposed on the surface of the substrate. The hinge may be positioned between the probe and the anchor. An angle may be formed between the probe and the anchor. The method may further include depositing an amount of solder on an area of the structure that spans from a portion of the probe to a portion of the anchor, and across the hinge. The method may further include removing the layer of sacrificial material. The method may further include reshaping the deposited solder by executing a solder reflow process on the structure. The reshaping may cause the probe to rotate about the hinge to reduce the angle between the probe and the anchor.

In some examples, a method of forming a device is generally described. The method may include disposing a layer of sacrificial material on a surface of a substrate of an electronic device. The method may further include disposing a layer of probe material on the layer of the sacrificial material. The method may further include forming a probe on the substrate using the layer of probe material. The method may further include disposing a hinge on the layer of sacrificial material and adjacent to a base of the probe. The method may further include disposing an anchor on the substrate and adjacent to the hinge, such that the hinge may be positioned between the probe and the anchor. The probe, the hinge, and the anchor may be arranged linearly. An angle may be formed between the probe and the anchor. The method may further include depositing an amount of solder on an area that spans from a portion of the probe to a portion of the anchor, and across the hinge. The method may further include removing the layer of sacrificial material. The method may further include reshaping the deposited solder by executing a solder reflow process on the electronic device. The reshaping may cause the probe to rotate about the hinge to reduce the angle between the probe and the anchor.

In some examples, an electronic device comprising a plurality of probes is generally described. The electronic device may include an integrated circuit, a substrate, and the plurality of probes. The plurality of probes may be perpendicular to the substrate and coupled to the integrated circuit. For each probe, a solder bump may be formed between the probe and an anchor, where the anchor may be attached to the substrate, and a hinge may be positioned between the probe and the anchor. For each probe, the solder bump may be attached to the probe, the hinge, and the anchor. For each probe, the solder bump may be formed by a solder reflow process on an amount of solder deposited on the probe, the hinge, and the anchor prior to the solder reflow process. For each probe, the solder reflow process causes the solder deposited on the probe, the hinge, and the anchor to reshape into the solder bump. For each probe, the reshape of the deposited solder causes the probe to rotate about the hinge to form a right angle with the anchor, such that the probe may be perpendicular to the substrate.

Further features as well as the structure and operation of various embodiments are described in detail below with reference to the accompanying drawings. In the drawings, like reference numbers indicate identical or functionally similar elements.

DETAILED DESCRIPTION

Micro-needles fabrication based on top-down etching may impose some limitations, such as limitations on an aspect ratio of the micro-needles, difficulty in fabricating micro-needles of different length at each fabrication instance, difficulty to embed electronics or electrodes onto each micro-needle, difficult to create micro-fluidic channels which are not straight within the micro-needles, and difficult to make the micro-needles out of composite materials. Thus, there is a need for a micro-needle fabrication process that may address these limitations.

To be described in more detail below, a planar fabrication of micro-needles may address at least some of the above limitations imposed by the top-down etching approach. Planar fabrication of micro-needles provides flexibility on the aspect ratio of the micro-needles due to using etching processes such as lithography to shape the micro-needles, and thus, micro-needles of different length may be easily formed compared to top-down etching approaches. Further, planar fabrication of micro-needles provides flexibility in a fabrication process of micro-needles and devices formed with micro-needles, by allowing electronics or electrodes to be embedded onto each micro-needle using common back end of line (BEOL) process, allowing micro-fluidic channels of various shapes and turns to be created, and allowing composite-material micro-needles to be made.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

Figure 1A:
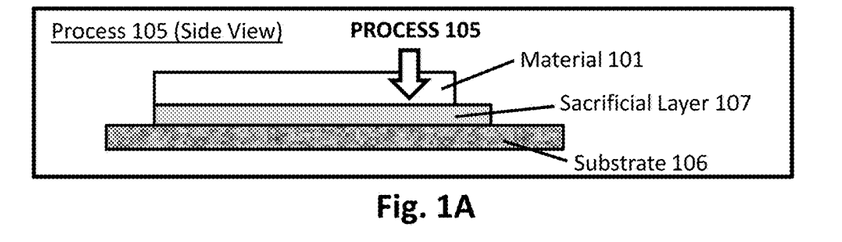
FIG. 1A illustrates a side view of an example process of a planar fabrication of micro-needles, in one embodiment.
Figure 1B:
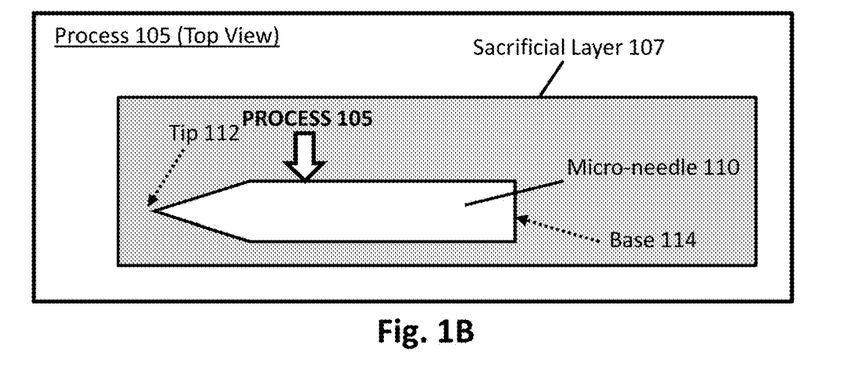
FIG. 1B illustrates a top view of an example process of a planar fabrication of micro-needles, in one embodiment.

FIG. 1A and FIG. 1B illustrate a side view and a top view, respectively, of an example process 105 of a planar fabrication of micro-needles, in one embodiment. The process 105 may be a process to form a micro-needle or probe, such as lithography, plasma etching, metal lift-off, metal wiring with dielectric stack, isotropic wet etch, and/or other fabrication processes. The process 105 is applied on a layer of probe material 101 disposed on top (e.g., directly on top) of a sacrificial layer 107, where the sacrificial layer 107 is formed with sacrificial materials such as polysilicon or oxide. The sacrificial layer 107 is formed on top (e.g., directly on top) of a surface of a substrate 106. The layer of probe material 101 may be disposed on the sacrificial layer 107 such that the layer of probe material 101 may be laid on a first plane that is parallel to a second plane in which the sacrificial layer 107 is laid on. A length of the micro-needle 110 may be parallel to a plane in which the substrate 106 is laid. The application of the process 105 on the probe material 101 may form a probe or a micro-needle 110 of a particular shape with particular dimensions. In some examples, the substrate 106 may be a substrate or wafer of a semiconductor chip or electronic device, such that the process 105 may be applied to form the micro-needle 110 directly on the semiconductor chip or the electronic device. As a result of the application of the process 105, the formed micro-needle 110 may include a tip 112 and a base 114. The probe material 101 of the micro-needle 110 may be silicon, metal, polymer, glass, composite materials, and/or other materials. The micro-needle 110 may be three-dimensional, and example dimensions of the micro-needle 110 may include approximately 30-1,000 microns (µm) in height or length, a base diameter of approximately 50-30 µm, and a tip diameter of approximately 1-50 µm. In some examples, the micro-needle 110 may be hollow such that the micro-needle 110 may be used to transfer fluids, such as medication, from the base 114 to the tip 112 of the micro-needle 110. In some examples, the micro-needle 110 may be embedded with various electrical components such as sensors, wires, electrodes, and/or other electrical components.

Figure 1C:
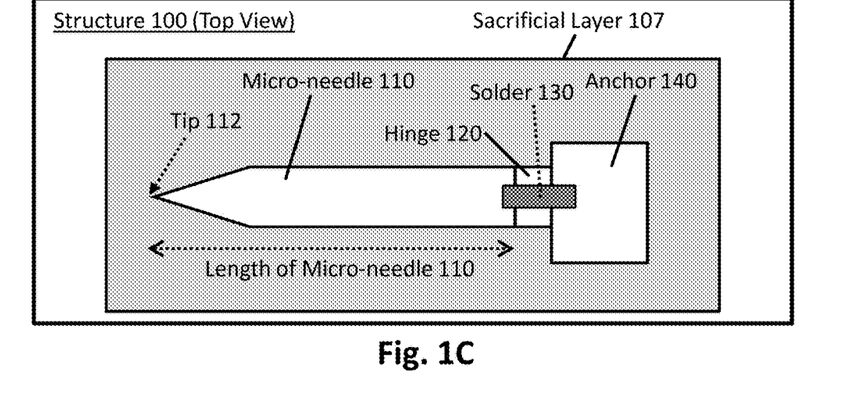
FIG. 1C illustrates an example structure, in a top view, that facilitates planar fabrication of micro-needles, in one embodiment.
Figure 1D:
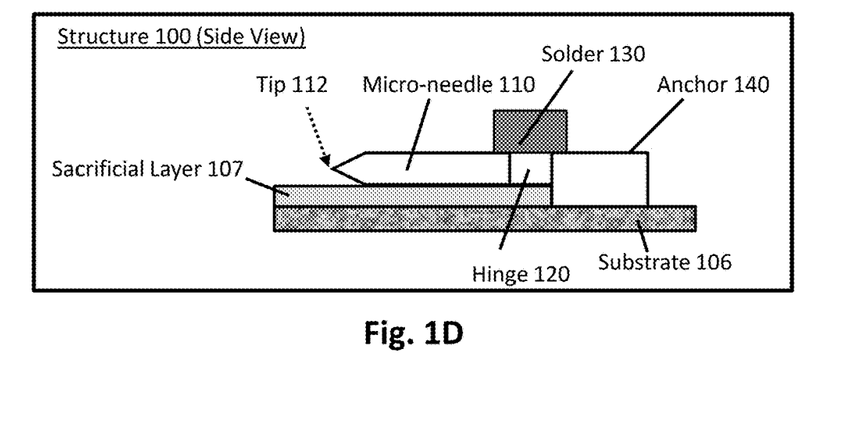
FIG. 1D illustrates an example structure, in a side view, that facilitates planar fabrication of micro-needles, in one embodiment.

FIG. 1C and FIG. 1D illustrate an example structure, in a top view and a side view, respectively, that facilitates planar fabrication of micro-needles, in one embodiment. A structure 100 may be formed on the substrate 106 and/or sacrificial layer 107. A hinge 120 may be disposed on the sacrificial layer 107 and adjacent to the base 114 of the micro-needle 110, where at least a portion of the hinge 120 may be attached to the micro-needle 110. As such, the micro-needle 110 and the hinge 120 may be on top of the sacrificial layer 107. An anchor 140 may be disposed on the substrate 106 and adjacent to the hinge 120, such that the hinge 120 is located between the base 114 of the micro-needle 110 and the anchor 140, where at least a portion of the anchor 140 may be attached to the hinge 120. The anchor 140 may be attached to the surface of the substrate 106, and the micro-needle 110 and the hinge 120 may not be attached to the substrate 106. The structure 100 may include the micro-needle 110, the hinge 120, and the anchor 140 arranged linearly. The hinge 120 may be made of a flexible, or a low modulus material, such as thin (e.g., 0.5 µm-2 µm) metal including aluminum, copper, parylene (at 1 µm-20 µm), polyimide (at 1 µm-10 µm), epoxy-based negative photoresist such as SU-8 (at 2 µm-90 µm), or other low modulus materials. The anchor 140 may be any material that does not remain attached to the sacrificial layer 107 if the sacrificial layer 107 is removed. In the example, the sacrificial layer 107 may be polysilicon, and the anchor 140 may be oxide, nitride, or aluminum, or other materials that does not remain attached to polysilicon in a removal process (further described below).

An amount of solder 130 may be deposited on an area of the structure 100 that spans from a portion of the micro-needle 110, across the hinge 120, to a portion of the anchor 140, such that the deposited solder 130 is in contact with the micro-needle 110, the hinge 120, and the anchor 140. The amount of solder 130 to be deposited is based on properties of the hinge 120, such as a length, width, thickness, material, bending moment, and/or other properties of the hinge 120. In an example, the hinge 120 may be made from SU-8 and may have a thickness of 10 µm, a length of 100 µm, a width of 30 µm. Based on this set of example dimensions of the hinge 120, the solder 130 deposited on the structure 100 may have a thickness of 40 µm, length of 40 µm, and a width of 40 µm. In an example, a width of the anchor 140 may be as least the width of the hinge 120 and/or the width of the solder 130. In an example, the solder 130 is disposed on the structure 100 prior to removing the sacrificial layer 107.

Figure 2A:
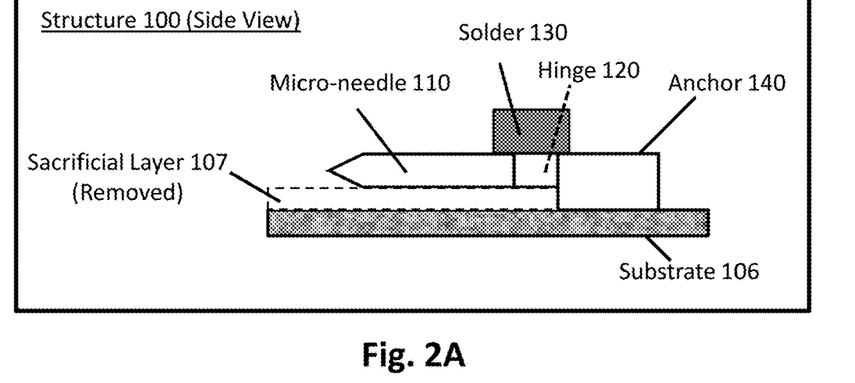
FIG. 2A illustrates an example structure, in a side view, that facilitates planar fabrication of micro-needles, in one embodiment.

FIG. 2A illustrates the example structure 100, in a side view, that facilitates planar fabrication of micro-needles, in one embodiment. As shown in FIG. 2A, the sacrificial layer 107 may be removed from the substrate 106. In an example where the sacrificial layer 107 is polysilicon, xenon difluoride ($XeF_2$) may be used to remove the sacrificial layer 107 from the structure 100 and/or the substrate 106. Without the sacrificial layer 107, the structure 100 may be attached to the substrate 106 based on the anchor 140 being attached to the structure 106. In some examples, the structure 100 may be removed from the substrate 106 and may be disposed on a new piece of substrate. In some examples, the structure 100 may be bonded or assembled on another piece of substrate, a semiconductor chip, or a device. In an example, if the micro-needle 110 is being fabricated directly on a semiconductor chip or a device that includes the substrate 106, the removal of the structure 100 may be unnecessary.

Figure 2B:
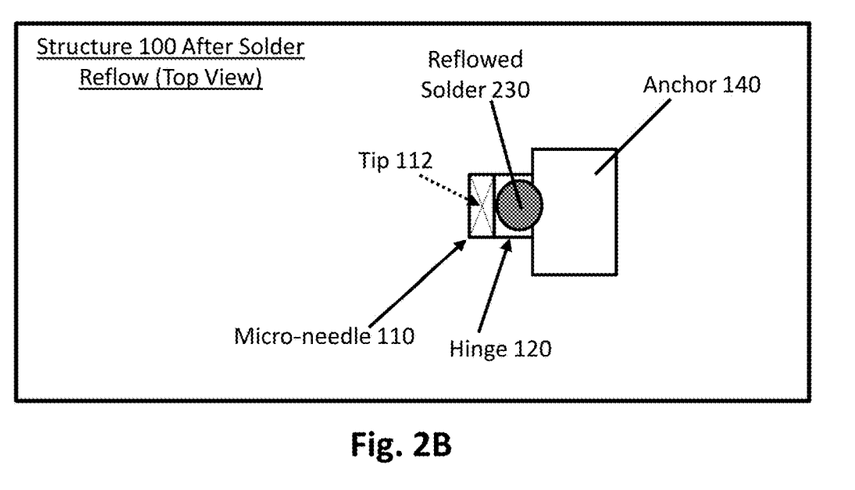
FIG. 2B illustrates an example structure, in a top view, after a solder reflow process of a planar fabrication of micro-needles, in one embodiment.
Figure 2C:
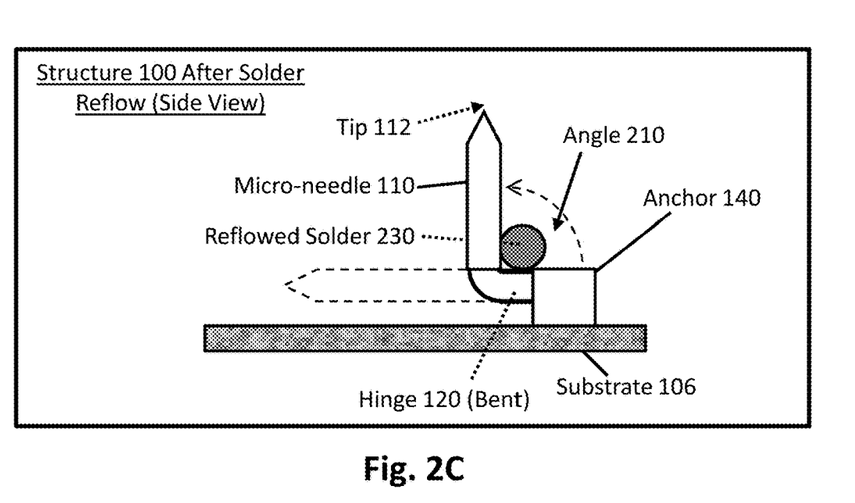
FIG. 2C illustrates an example structure, in a side view, after a solder reflow process of a planar fabrication of micro-needles, in one embodiment.

FIG. 2B and FIG. 2C illustrate the example structure 100, in a top view and side view, respectively, after a solder reflow process of a planar fabrication of micro-needles, in one embodiment. The solder reflow process may include a first phase that subjects the structure 100 and the solder 130 to controlled heat in an environment or an apparatus, then a second phase of cooling the structure 100 and the solder 130. For example, in the first phase, the structure 100 may be placed in a reflow oven, under infrared lamp, or be subjected to hot air of a controlled temperature, that will cause the deposited solder 130 to melt without damaging any parts of the structure 100. The controlled temperature and the temperature ramping profile may depend on the materials of the micro-needle 110, the hinge 120, and the anchor 140. In some examples, the controlled temperature may be approximately 220° C. to 250° C., and the structure 100 may be subjected to the controlled temperature for a specified amount of time, such as approximately 1 to 10 minutes. After the first phase, the structure 100 with the melted solder may be removed from the controlled heat, and may undergo the second phase to cool the structure 100 and the melted solder. The second phase may include placing the structure 100 with the melted solder in a relatively cool environment, such as room temperature or in a cooling apparatus that provides cooled air to cool the melted solder.

The cooling of the melted solder may cause the solder 130 to tense and harden, and the tension and hardening may deform or reshape the melted solder into a new shape, such as shrinking the melted solder into a substantially spherical piece of reflowed solder, or solder bump 230. In one embodiment, since the melted solder is attached to a portion of the micro-needle 110, the hardening and reshaping of the melted solder will lift the tip 112 of the micro-needle 110 upward, and out-of-plane from a plane of the substrate 106. In other words, the hardening and reshaping of the melted solder causes the tip 112 of the micro-needle 110 to rotate upward about the hinge 120 and away from the surface of substrate 106, with the hinge 120 acting as a pivot of the rotation. The upward rotation of the micro-needle 110 about the hinge 120 causes an angle between the micro-needle 110 and the hinge 120 to reduce. For example, prior to the solder reflow process, the micro-needle 110 was arranged to have a straight angle (e.g., 180 degrees) with the anchor 140. As a result of the solder reflow process, the upward rotation of the micro-needle 110 about the hinge 120 reduces the angle between the micro-needle 110 and the anchor 140 to an angle 210 that is less than the straight angle. Further, the removal of the sacrificial layer 107 produces a gap between the substrate 106 and the combination of the micro-needle 110 and the hinge 120, such that the solder reflow process may cause the micro-needle 110 to rotate upward without any hindrance. The second phase to cool the melted solder may continue until the angle 210 is 90-degrees, or a right angle. When the angle 210 is a right angle, a tension of the reflowed solder 230 is at least balanced, or larger than, a bending moment of the hinge 120. Thus, after a completion of the reshaping of the melted solder, the micro-needle 110 is out-of-plane from the substrate 106, and is perpendicular to the hinge 120, the anchor 140, and/or the substrate 106. The hardened reflowed solder 230 may provide structural strength to support the now out-of-plane micro-needle 110.

In an example, the amount or volume of solder 130 deposited on the structure 100 prior to the solder reflow process is substantially the same as a volume of the reflowed solder 230 after the solder reflow process. In the example above where the solder 130 deposited on the structure 100 has a thickness of 40 μm, length of 40 μm, and a width of 40 μm, a radius of the reflowed solder 230 may be approximately 20 μm.

Figure 3A:
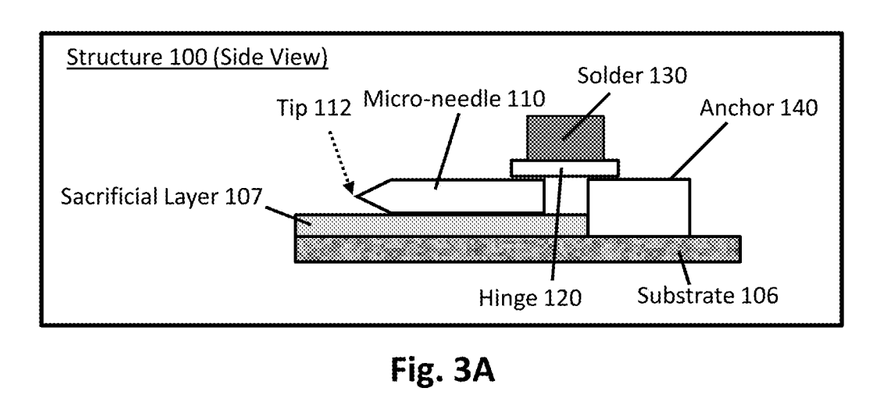
FIG. 3A illustrates an example structure, in a side view, that facilitates planar fabrication of micro-needles, in one embodiment.

FIG. 3A illustrates an example structure, in a side view, that facilitates planar fabrication of micro-needles, in one embodiment. In the example shown in FIG. 3A, the hinge 120 may be disposed directly on top of a portion of the micro-needle 110 and on top of a portion of the anchor 140. For instance, the hinge 120 may bridge a gap or void between the base 114 of the micro-needle 110 and the anchor 140. Thus, the micro-needle 110 may be directly on top of the sacrificial layer 107, the anchor 140 may directly on top of the substrate 106, and the hinge 120 may not be in contact with, or may be separated from, the sacrificial layer 107 and the substrate 106. The solder 130 may be disposed directly on top of the hinge 120 without being in contact with the micro-needle 110 and the anchor 140.

Figure 3B:
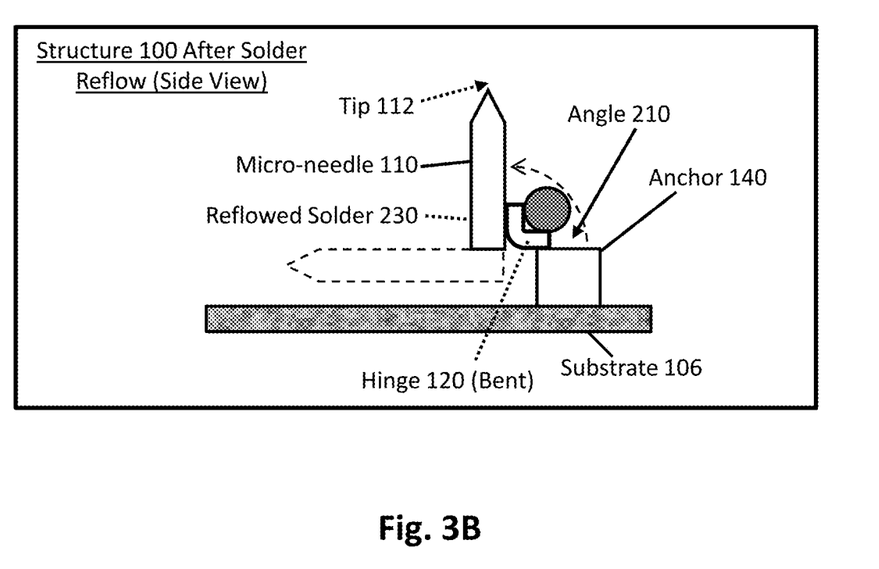
FIG. 3B illustrates an example structure, in a side view, after a solder reflow process of a planar fabrication of micro-needles, in one embodiment.

FIG. 3B illustrates an example structure, in a side view, after a solder reflow process of a planar fabrication of micro-needles, in one embodiment. The melting of solder 130 and the cooling of the melted solder, described above, may cause the solder 130 to tense and harden, and may deform or reshape the melted solder into the solder bump 230. Based on the melted solder being attached to the hinge 120 and not attached to the micro-needle 110 and anchor 140 (shown in FIG. 3A), the reshaping of the melted solder deforms or reshapes the hinge 120, such as by bending the hinge 120 to the angle 210. The bending of the hinge 120 causes the tip 112 of the micro-needle 110 to lift upward, and out-of-plane from a plane of the substrate 106.

Figure 4A:
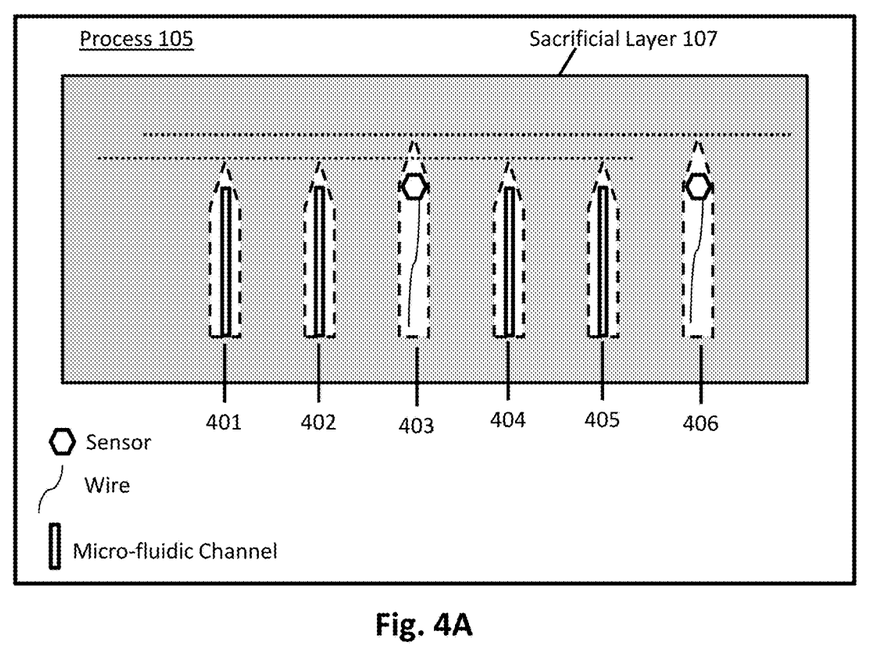
FIG. 4A illustrates a top view of an example process of a planar fabrication of micro-needles, in one embodiment.

FIG. 4A illustrates a top view of the example process 105 of a planar fabrication of micro-needles, in one embodiment. Typically, in a top-down etching approach, it may be difficult to fabricate and shape micro-needles and probes with heterogeneous integration of micro-fluidic channels and electronics, as the out-of-plane micro-needles and probes may be fragile and may not be compatible with typical bonding or assembly processes. In one embodiment, the methods in accordance with the present disclose provides flexibility to produce micro-needles and probes, which are heterogeneous, on a device in one fabrication instances. For example, micro-needles with different size, shape, embedded components, and/or applications, are referred to as heterogeneous micro-needles; probes with different size, shape, embedded components, and/or applications, are referred to as heterogeneous probes. In an example shown in FIG. 4A, the process 105 may be applied to form a plurality of micro-needles of different sizes (e.g., length, width, diameter) and shapes, for example, a set of heterogeneous micro-needles 401, 402, 403, 404, 405, 406. The process 105 may further include application of various etching and embedding steps to create micro-fluidic channels in particular micro-needles (e.g., see micro-needles 401, 402, 404, 405) and to embed electronics and sensors with accompanying connections such as wires (e.g., see micro-needles 403, 406). For example, the process 105 may be a planar micro-fabrication process forming micro-needles and/or probes with embedded micro fluidic channels, wires, electrodes, and may perform reactive-ion etching (RIE) to define a shape of the micro-needles or probes. The embedded micro-fluidic channels and electronics arrangements, or layout, may be different from among the micro-needles or probes and may be defined by etching processes such as lithography.

Figure 4B:
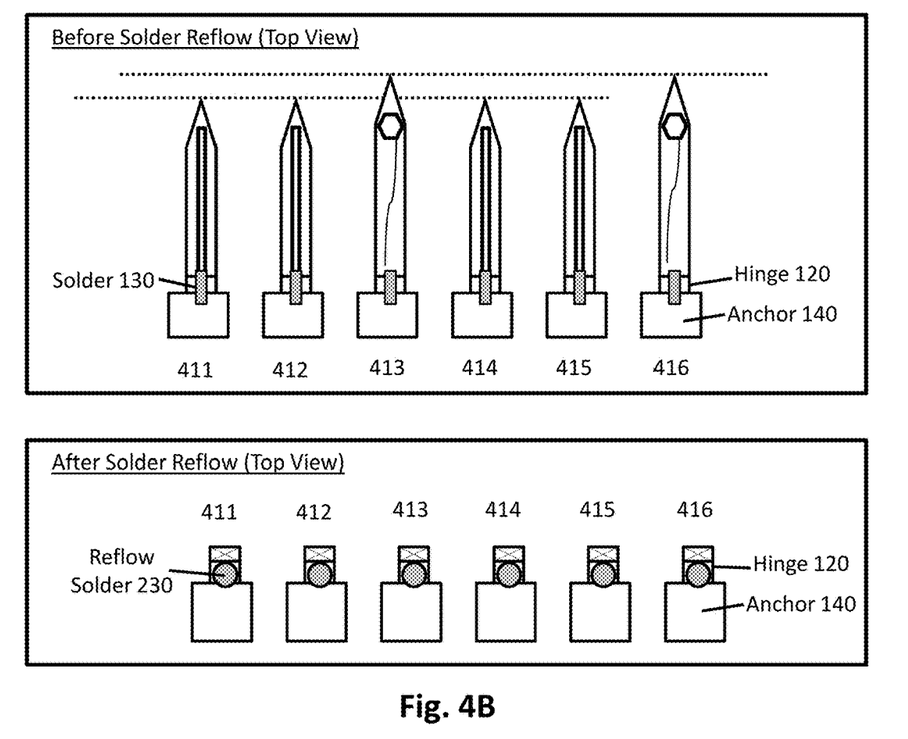
FIG. 4B illustrates a plurality of example structures, in a top view, before and after a solder reflow process of a planar fabrication of micro-needles, in one embodiment.

FIG. 4B illustrates a plurality of example structures corresponding to the set of heterogeneous micro-needles of FIG. 4A, in a top view, before and after a solder reflow process of a planar fabrication of micro-needles, in one embodiment. Each micro-needle among the set of heterogeneous micro-needles 401, 402, 403, 404, 405, 406 may be attached with respective hinge 120 and anchor 140 to form a set of heterogeneous structures 411, 412, 413, 414, 415, 416. Each structure among structures 411, 412, 413, 414, 415, 416 may be deposited with a respective amount of solder 130 (e.g., the amount being based on the material and a size of respective micro-needle and hinge). The heterogeneous structures 411, 412, 413, 414, 415, 416 may be subjected to the solder reflow process described above, and as a result of the solder reflow process, the micro-needles 401, 402, 403, 404, 405, 406 will be raised out-of-plane to an angle perpendicular with a corresponding hinge and/or an underlying substrate (not shown). To be described in more detail below, the heterogeneous set of micro-needles and probes may be formed directly on a device to produce a functional device with the heterogeneous set of micro-needles.

Figure 5A:
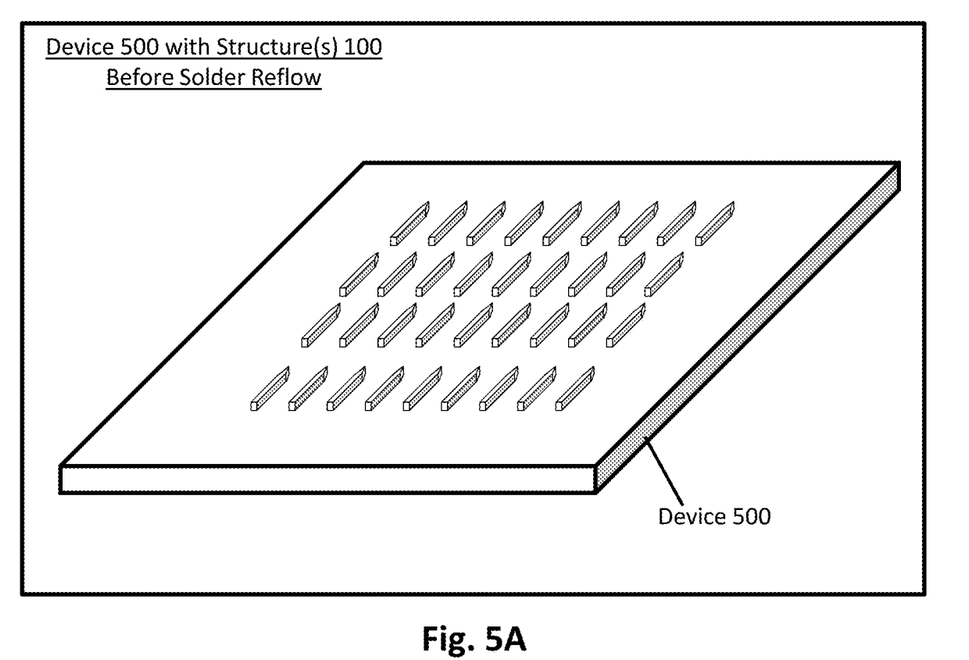
FIG. 5A illustrates an example device with a plurality of example structures before a solder reflow process of a fabrication of micro-needles, in one embodiment.
Figure 5B:
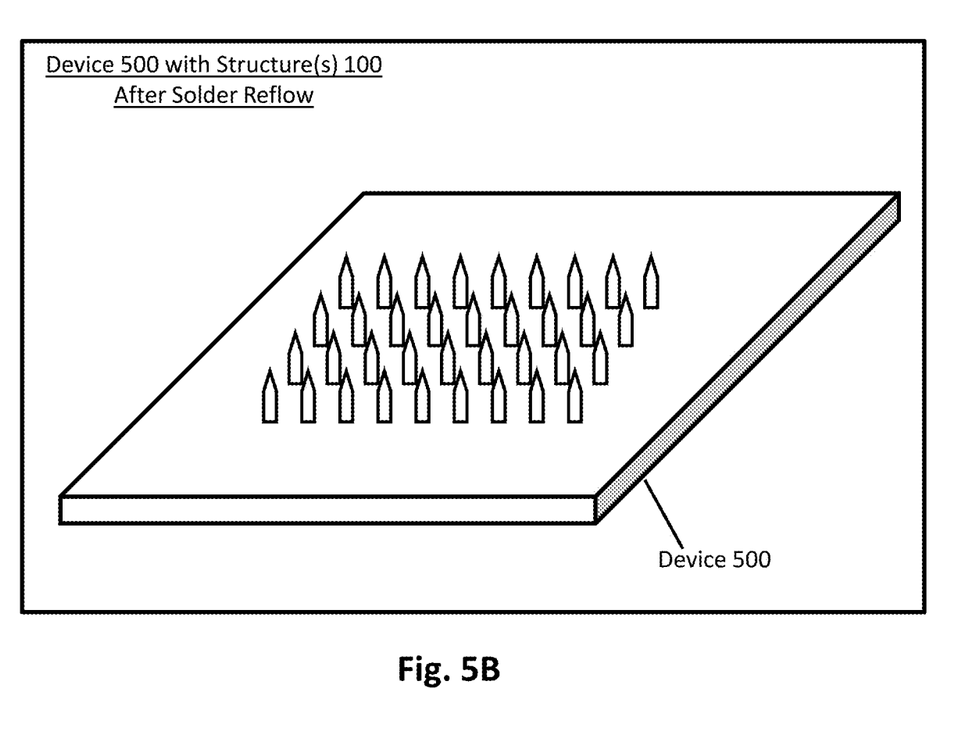
FIG. 5B illustrates an example device with a plurality of example structures after a solder reflow process of a planar fabrication of micro-needles, in one embodiment.

FIG. 5A illustrates an example device 500 with a plurality of example structures before a solder reflow process of a fabrication of micro-needles, in one embodiment. The device 500 may be a semiconductor chip or an electronic device including integrated circuits. In some applications, it may be desirable to integrate a set of heterogeneous micro-needles and/or probes on a semiconductor chip (e.g., device 500) to form a functional system, such as a multi-purpose system where medication can be delivered, electronic pulses may be administered, and electronic or chemical signals may be measured, using different types of micro-needles on the same chip. As described above, in an example shown by FIG. 4A and FIG. 4B, the methods in accordance with the present disclosure may produce heterogeneous micro-needles and probes that may carry electronic signals, be embedded with micro-fluidic channels, and/or be embedded with different metal wire routing, on a same device. In an example shown in FIG. 5A, a set of heterogeneous structures (e.g., heterogeneous structures 411, 412, 413, 414, 415, 416 in FIG. 4B) may be bonded or assembled to the device 500 in a planar configuration and as an additional top layer. In some examples, the structures may be bonded to the device 500 such that the structures are electronically coupled to the integrated circuits of the device 500. For example, if a particular probe of a particular structure is embedded with a sensor to detect changes to glucose levels in a bloodstream, the particular structure may be electronically coupled to a component, such as a light emitting diode (LED) indicator, of the integrated circuits of the device 500 during the bonding and prior to subjecting the device 500 to the solder reflow process. The device 500, with the bonded heterogeneous structures, may be subjected to the reflow solder process such that the micro-needles of the heterogeneous structures may raise out of plane to be perpendicular to the device 500, resulting in the device with heterogeneous micro-needles and/or probes shown in FIG. 5B. In some examples, an arrangement of the heterogeneous structures may be formed on the device 500 such that a minimum pitch (e.g., center-to-center spacing) between the micro-needles of the structures, along a longitudinal direction of the micro-needles, is determined based on the length of the micro-needles. For example, it may be desirable for the pitch between the micro-needles along the longitudinal direction of the micro-needles to be greater than the length of the micro-needles, such that each micro-needle may be raised without touching another micro-needle in the longitudinal direction. The pitch between the micro-needles along a traverse direction of the micro-needles formed on the device 500 may be less than the pitch along the longitudinal direction of the micro-needles.

Figure 6:
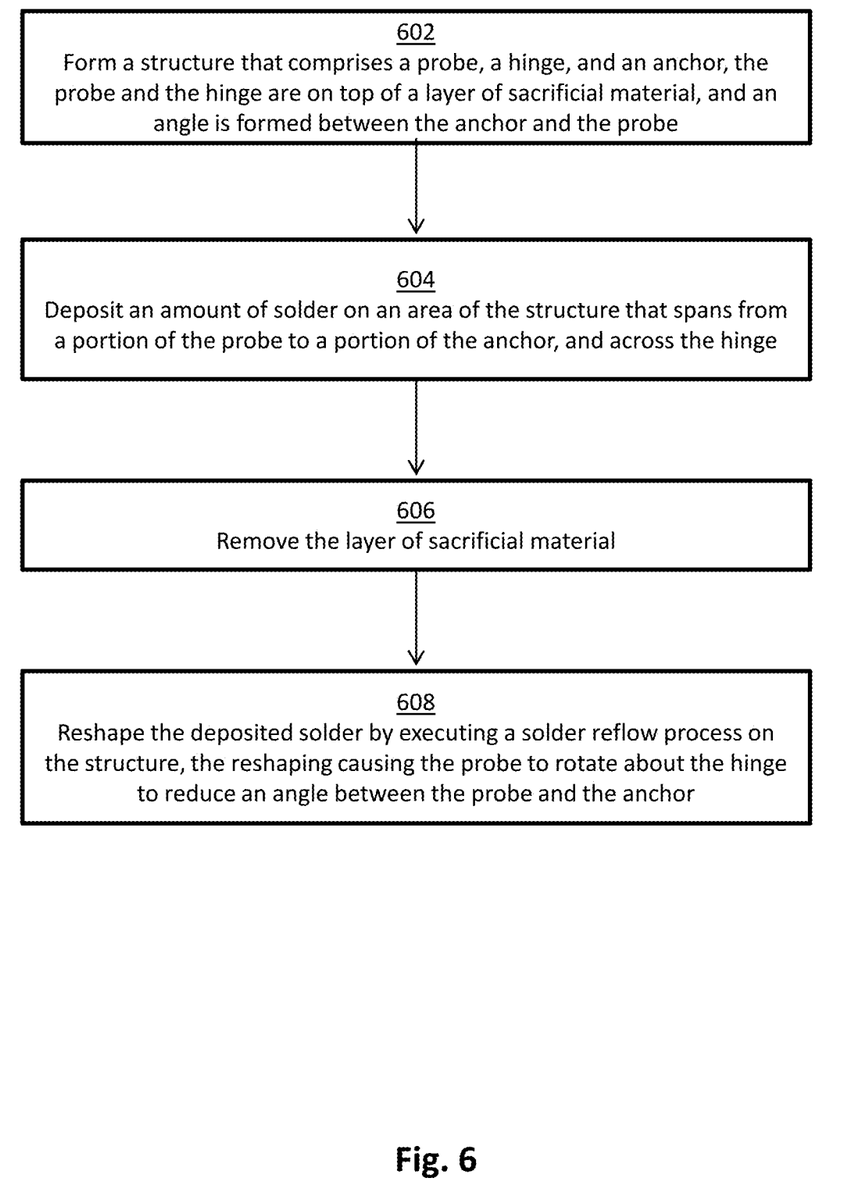
FIG. 6 illustrates a flow diagram relating to a process to implement planar fabrication of micro-needles, in one embodiment.

FIG. 6 illustrates a flow diagram relating to a process to implement a test environment with a thermal interface formed by condensate, arranged in accordance with at least some embodiments presented herein. The process in FIG. 6 may be implemented using, for example, system 100 discussed above. An example process may include one or more operations, actions, or functions as illustrated by one or more of blocks 602, 604, 606, and/or 608. Although illustrated as discrete blocks, various blocks may be divided into additional blocks, combined into fewer blocks, eliminated, or performed in parallel, depending on the desired implementation.

The processing may begin at block 602, where a structure is formed. The structure includes a probe, a hinge, and an anchor arranged linearly. The probe and the hinge are on top of a layer of sacrificial material. The layer of sacrificial material is on top of a surface of a substrate. The anchor is disposed on a surface of the substrate. The hinge is positioned between the probe and the anchor. An angle is formed between the probe and the anchor. The structure is parallel to the substrate. In some examples, the probe is formed using a technique selected from a group comprising lithography, plasma etching, metal lift-off, metal wiring with dielectric stack, and isotropic wet etch. In some examples, the probe may be a micro-needle. In some examples, the probe includes at least one of embedded electronics, electrodes, and micro-fluidic channels The processing may continue from block 602 to block 604. At block 604, an amount of solder is deposited on an area of the structure that spans from a portion of the probe to a portion of the anchor, and across the hinge. In some examples, the substrate is a substrate of the electronic device, and the solder reflow process is being executed on the electronic device with the structure. In some examples, the substrate is not a part of the electronic device, and the structure with the deposited solder is removed from the substrate prior to executing the solder reflow process. The removed structure with the deposited solder may be bonded with the electronic device prior to executing the solder reflow process, such that the solder reflow process is being executed on the electronic device and the structure with the deposited solder. The processing may continue from block 604 to block 606. At block 606, the layer of sacrificial material is removed.

The processing may continue from block 606 to block 608. At block 608, the deposited solder may be reshaped by an execution of a solder reflow process. The reshape of the deposited solder causes the probe to rotate about the hinge to reduce the angle between the probe and the anchor. The solder reflow process ends when the angle between the probe and the anchor is a right angle such that the probe is perpendicular to the substrate. In some examples, the structure is among a plurality of structures formed on the substrate, where each structure among the plurality of structures comprises a respective set of probe, hinge, and anchor. In some examples, the probes of the plurality of structures are heterogeneous.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
    forming a structure that comprises a probe, a hinge, and an anchor arranged linearly, the probe and the hinge are on top of a layer of sacrificial material, the layer of sacrificial material is on top of a surface of a substrate, the anchor is disposed on the surface of the substrate, the hinge is positioned between the probe and the anchor, and an angle is formed between the anchor and the probe;
    depositing an amount of solder on an area of the structure that spans from a portion of the probe to a portion of the anchor, and across the hinge;
    removing the layer of sacrificial material; and
    reshaping the deposited solder by executing a solder reflow process on the structure, wherein reshaping the deposited solder causes the probe to rotate about the hinge to reduce the angle between the probe and the anchor.

2. The method of claim 1, further comprising forming the probe using a technique selected from a group comprising lithography, plasma etching, metal lift-off, metal wiring with dielectric stack, and isotropic wet etch.

3. The method of claim 1, wherein the probe is a micro-needle.

4. The method of claim 1, further comprising:
    removing the structure with the deposited solder from the substrate prior to executing the solder reflow process; and
    bonding the structure with the deposited solder on an electronic device prior to executing the solder reflow process, and the solder reflow process is being executed on the electronic device and the structure with the deposited solder.

5. The method of claim 1, wherein the probe comprises at least one of embedded electronics, electrodes, and micro-fluidic channels.

6. The method of claim 1, wherein the substrate is a substrate of an electronic device, and the solder reflow process is being executed on the electronic device with the structure.

7. The method of claim 1, wherein the structure is among a plurality of structures formed on the substrate, each structure among the plurality of structures comprises a respective set of probe, hinge, and anchor arranged linearly, each probe forms an angle with a corresponding anchor, and the method further comprising:

depositing respective amount of solder on each structure; and
    reshaping the solder deposited on each structure by executing the solder reflow process on the plurality of structures, wherein reshaping the solder deposited on each structure causes each probe to rotate about the corresponding hinge to reduce the angle between each probe and the corresponding anchor.

8. The method of claim 7, wherein the probes of the plurality of structures are heterogeneous.

9. The method of claim 1, wherein the reshaping ends when the angle between the probe and the anchor is a right angle such that the probe is perpendicular to the substrate.

10. A method comprising:
    disposing a layer of sacrificial material on a surface of a substrate of an electronic device;
    disposing a layer of probe material on the layer of sacrificial material;
    forming a probe on the substrate using the layer of probe material;
    disposing a hinge on the layer of sacrificial material and adjacent to a base of the probe;
    disposing an anchor on the substrate and adjacent to the hinge, such that the hinge is positioned between the probe and the anchor, and the probe, the hinge, the anchor are arranged linearly, and an angle is formed between the probe and the anchor;
    depositing an amount of solder on an area that spans from a portion of the probe to a portion of the anchor, and across the hinge;
    removing the layer of sacrificial materials; and
    reshaping deposited solder by executing a solder reflow process on the electronic device, wherein the reshaping the deposited solder causes the probe to rotate about the hinge to reduce the angle between the probe and the anchor.

11. The method of claim 10, wherein forming the probe comprises applying a technique selected from a group comprising lithography, plasma etching, metal lift-off, metal wiring with dielectric stack, and isotropic wet etch.

12. The method of claim 10, wherein the probe is a micro-needle.

13. The method of claim 10, wherein the probe comprises at least one of embedded electronics, electrodes, and microfluidic channels.

14. The method of claim 10, wherein the probe is among a plurality of probes formed on the layer of sacrificial material, the method further comprising:
    disposing a plurality of hinges on the sacrificial material, each hinge being adjacent to a base of a corresponding probe among the plurality of probes;
    disposing a plurality of anchors on the substrate, each anchor being adjacent to a hinge among the plurality of hinges, such that each hinge is positioned between the corresponding probe and a corresponding anchor, and an angle is formed between each probe and the corresponding anchor, wherein each set of probe, hinge, and anchor are arranged linearly to form a structure;
    depositing respective amount of solder on each structure; and
    reshaping the solder deposited on each structure by executing the solder reflow process on the electronic device, wherein the reshaping of the solder deposited on each structure causes each probe to rotate about a corresponding hinge to reduce the angle between each probe and the corresponding anchor.

15. The method of claim 14, wherein the probes of the plurality of structures are heterogeneous.

16. The method of claim 10, wherein the reshaping ends when the angle between each probe and a corresponding anchor is a right angle such that each probe is perpendicular to the substrate.

17. An electronic device comprising:
an integrated circuit;
a substrate;
a plurality of probes perpendicular to the substrate and coupled to the integrated circuit, wherein, for each probe:
  a solder bump is formed between the probe and an anchor, wherein the anchor is attached to the substrate, and a hinge is positioned between the probe and the anchor;
  the solder bump is attached to the probe, the hinge, and the anchor;
  the solder bump is formed by a solder reflow process on an amount of solder deposited on the probe, the hinge, and the anchor prior to the solder reflow process;
  the solder reflow process causes the solder deposited on the probe, the hinge, and the anchor to reshape into the solder bump; and
  the reshape of the deposited solder causes the probe to rotate about the hinge to form a right angle with the anchor, such that the probe is perpendicular to the substrate.

18. The electronic device of claim 17, wherein each probe is a micro-needle.

19. The electronic device of claim 17, wherein each probe comprises at least one of embedded electronics, electrodes, and micro-fluidic channels.

20. The electronic device of claim 17, wherein the plurality of probes are heterogeneous.

* * * * *